United States Patent [19]
Bachmann et al.

[11] Patent Number: 4,963,574
[45] Date of Patent: * Oct. 16, 1990

[54] N-CYANOISOTHIOUREA COMPOUNDS USEFUL IN PEST CONTROL

[75] Inventors: Markus Bachmann, Sisseln; Laurenz Gsell, Basle; Hanspeter Fischer, Bottmingen, all of Switzerland

[73] Assignee: Ciba-Geigy Corporation, Ardsley, N.Y.

[*] Notice: The portion of the term of this patent subsequent to Oct. 16, 2007 has been disclaimed.

[21] Appl. No.: 156,113

[22] Filed: Feb. 16, 1988

[30] Foreign Application Priority Data

Feb. 24, 1987 [CH] Switzerland ............... 687/87

[51] Int. Cl.$^5$ ............ A61K 31/44; A61K 31/34
[52] U.S. Cl. ............ 514/357; 514/415; 514/428; 514/461; 546/330; 548/505; 548/561; 549/492
[58] Field of Search ............ 514/357, 408, 415, 461, 514/428; 546/330; 548/505, 561; 549/492

[56] References Cited

FOREIGN PATENT DOCUMENTS 234064 10/1987 Japan ............... 546/330

OTHER PUBLICATIONS

Chemical Abstracts, Abstract No. 187,063Z, vol. 95, No. 21, p. 636, Nov. 23, 1981, Marishita Pharmaceutical.
Chemical Abstracts, Abstract No. 142,993e, vol. 85, No. 19, p. 514, Nov. 8, 1976, Petersen.

Primary Examiner—Mary C. Lee
Assistant Examiner—Zinna N. Davis
Attorney, Agent, or Firm—Kevin T. Mansfield; Edward M. Roberts

[57] ABSTRACT

Use of a compound of formula

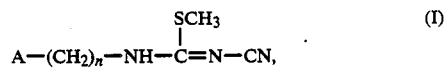

wherein A is an aromatic-heterocyclic ring which contains an oxygen or nitrogen atom, and n is 1 or 2, for controlling insects and plant-destructive nematodes and to a composition containing such a compound. The compounds of this invention are particularly suitable for controlling sucking insects.

6 Claims, No Drawings

N-CYANOISOTHIOUREA COMPOUNDS USEFUL IN PEST CONTROL

The present invention relates to the use of specific N-cyanoisothiourea derivatives for controlling pests and to pesticidal compositions which contain these compounds as active component.

In one of its aspects, the present invention relates to the use of a compound of formula I

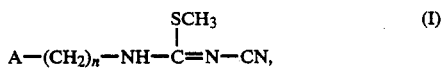

wherein A is an aromatic-heterocyclic ring which contains an oxygen or nitrogen atom, and n is 1 or 2, for controlling insects and plant-destructive nematodes.

Within the scope of the proposed utility of this invention, those compounds of formula I are preferred in which A is pyridyl, furanyl, indolyl or pyrrolyl, and/or those compounds of formula I wherein n is 1. On account of their pronounced pesticidal activity, particularly preferred compounds of formula I for the proposed utility are those wherein A is pyrid-2-yl, pyrid-3-yl, furan-2-yl, indol-3-yl or pyrrol-3-yl.

In another of its aspects, the present invention relates to novel compositions for controlling harmful insects and plant-destructive nematodes, which compositions contain, as active component, at least one compound of formula I

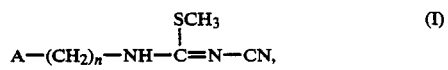

wherein A is an aromatic-heterocyclic ring which contains an oxygen or a nitrogen atom and n is 1 or 2.

Preferred compositions of the invention contain, as active component, a compound of formula I, wherein A is pyridyl, furanyl, indolyl or pyrrolyl and/or n is 1. Particularly preferred compositions are those which contain a compound of formula I, wherein A is pyrid-2-y, pyrid-3-yl, furan-2-yl, indol-3-yl or pyrrol-3-yl.

N-Cyanoisothioureas which fall within the scope of formula I, their preparation and the use thereof as medicaments for treating ulcers have already been disclosed in Japanese patent publication Kokai No. 62-234064.

Surprisingly, it has been found that the compounds of formula I of this invention have excellent insecticidal and nematocidal properties while being well tolerated by plants and having low toxicity to warm-blooded animals. They are particularly suitable for controlling insects that attack plants and animals. In this connection attention is drawn to the very low toxicity of the compounds of this invention to fish.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

The good pesticidal activity of the compounds of this invention corresponds to a mortality of at least 50–60% of the above pests.

The compounds of formula I can also be used for controlling plant-destructive feeding insects in ornamentals and crops of useful plants. The compounds of formula I are very effective against larval insect stages and nymphs. The compounds of formula I can also be used very successfully against plant-destructive cicadas, especially in rice crops. Quite generally, it has been found that the compounds of formula I are distinguished by a very pronounced systemic action as well as contact action against sucking insects, especially against insects of the families Delphacidae and Cicadellidae (e.g. *Nilaparvata lugens, Laodelphax striatellus* and *Nephotettix cincticeps*), control of which with known pesticides has hitherto only been achieved with difficulty.

The compounds of this invention are also suitable for controlling soil nematodes which parasiticise on roots, for example those of the genera Heterodera and Globodera (cyst nematodes), Meloidogyne (root-knot nematodes) as well as of the genera Radopholus, Pratylenchus, Tylenchulus, Longidorus, Trichodorus and Xiphenema. Further, the compounds of this invention are effective against the nematodes of the genera Ditylenchus (stem parasites), Aphelenchoides (leaf nematodes) and Anguina (seed-gall nematodes). With the compounds of formula I it is possible to effect successful control preferably of plant nematodes of the genera Meloidogyne such as *Meloidogyne incognita*, as well as Heterodera such as *Heterodera glycines* (soybean cyst nematodes) and also of the genus Globodera, e.g. *Globodera rostochiensis* (potato cyst nematode), and representatives of plant-destructive endoparasites such as *Pratylenchus penetrans* or *Radopholus similis*, and ectoparasites such as Trichodorus spp. and Xiphinema spp. The nematicidal activity of the compounds of the invention is advantageously accompanied by a low phytotoxicity, whereby the generally desirable lessening of risk to the environment is especially taken into account.

The following compounds which are disclosed in the aforementioned Japanese patent publication Kokai No. 62-234064 and which fall under the scope of formula I are particularly suitable for the purposes of this invention:

| Compound | | m.p. [°C.] |
|---|---|---|
| 1 | ![pyridine-CH2-NH-C(SCH3)=N-CN] | 155–156 |
| 2 | ![pyridine-CH2-NH-C(SCH3)=N-CN] | 116–117 |
| 3 | ![pyridine-CH2-NH-C(SCH3)=N-CN] | 167–168 |
| 4 | ![furan-CH2-NH-C(SCH3)=N-CN] | 134–135 |

-continued

| Compound | | m.p. [°C.] |
|---|---|---|
| 5 | pyridyl-(CH₂)₂—NH—C(SCH₃)=N—CN | 97–98 |
| 6 | indolyl-(CH₂)₂—NH—C(SCH₃)=N—CN | 169–170 |

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and Bacillus thuringiensis preparations.

The compounds of formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, New Jersey, 1979; Dr. Helmut Stache, "Tensid Taschenbuch" (Handbook of Surfactants), Carl Hauser Verlag, Munich/Vienna, 1981.

The pesticidal compositions usually contain—based on weight—0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients for obtaining special effects.

EXAMPLE 1

Preparation of N-cyano-S-methyl-N'-[2-(1-methylpyrrol-2-yl)ethyl-]isothiourea 6.21 g of 2-(2-aminoethyl)-1-methylpyrrole, 7.31 g of dimethyl-N-cyanodithioiminocarbonate, 50 ml of acetonitrile and 50 mg of 4-dimethylaminopyridine are combined and heated for 2 hours under reflux. After cooling to 10° C., the reaction mixture is filtered with suction and the filter residue is washed with diethyl ether and dried in the air, affording the title compound of formula

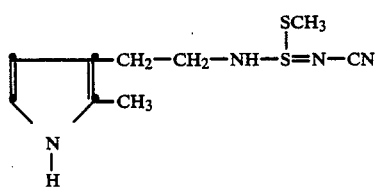

with a melting point of 182°–184° C. (compound 7).

The following compounds of formula I are also prepared in a manner analogous to that described in this Example:

| Compound | | m.p. [°C.] |
|---|---|---|
| 8 | ![structure with SCH3, CH2-CH2-NH-C=N-CN on pyridine ring] | 98,5-100 |
| 9 | ![structure with SCH3, CH2-CH2-NH-C=N-CN on pyrrole ring] | 117–118 |
| 10 | ![structure with SCH3, CH2-NH-C=N-CN on furan ring] | 135–136 |

EXAMPLE 2

Formulations for compounds of formula I (throughout, percentages are by weight)

| 1. Wettable powders | (a) | (b) | (c) |
|---|---|---|---|
| a compound of the Examples | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 67% | 27% | — |

The active compound is thoroughly mixed with the adjuvants and the mixture is thoroughly ground in a suitable mill, affording wettable powders which can be diluted with water to give suspensions of the desired concentration.

| 2. Emulsifiable concentrate | (a) | (b) |
|---|---|---|
| a compound of the Examples | 10% | 10% |
| octylphenol polyethylene glycol ether (4–5 mol of ethylene oxide) | 3% | — |
| calcium dodecylbenzenesulfonate | 3% | — |
| castor oil polyglycol ether (36 mol of ethylene oxide) | 4% | — |
| castor oil thioxilate | — | 25% |
| cyclohexanone | 30% | — |
| butanol | — | 15% |
| xylene mixture | 50% | — |
| ethyl acetate | — | 50% |

Emulsions of any required concentration can be obtained from this concentrate by dilution with water.

| 3. Dusts | (a) | (b) |
|---|---|---|
| a compound of the Examples | 5 | 8% |
| talcum | 95% | — |
| kaolin | — | 92% |

Ready-for-use dusts are obtained by mixing the active compound with the carrier, and grinding the mixture in a suitable mill.

| 4. Extruder granulate | |
|---|---|
| a compound of the Examples | 10% |
| sodium lignosulfonate | 2% |
| carboxymethylcellulose | 1% |

-continued

| 4. Extruder granulate | |
|---|---|
| kaolin | 87% |

The active compound is mixed and ground with the adjuvants, and the mixture is subsequently moistened with water. The mixture is extruded and then dried in a stream of air.

| 5. Coated granulate | |
|---|---|
| a compound of the Examples | 3% |
| polyethylene glycol (mol. wt. 200) | 3% |
| kaolin | 94% |

The finely ground active compound is uniformly applied, in a mixer, to the kaolin moistened with polyethlene glycol. Non-dusty coated granulates are obtained in this manner.

| 6. Suspension concentrate | |
|---|---|
| a compound of the Examples | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32 |

The finely ground active compound is intimately mixed with the adjuvants, giving a suspension concentrate from which suspensions of any desired concentration can be obtained by dilution with water.

EXAMPLE 3

Contact action against *Aphis craccivora*

Before the start of the test, 4- to 5-day old pea seedlings reared in 20 ml pots are each populated with about 200 insects of the species *Aphis craccivora*. The treated plants are sprayed direct to drip point 24 hours later with an aqueous formulation containing 400 ppm of the test compound. Two plants are used for each test compound at its given concentration. A mortality count is made after 3 and 5 days. The test is carried out at 21°-22° C. and at a relative humidity of about 60%.

In this test, compound 1 effects 90 to 100% mortality.

EXAMPLE 4

Contact action against *Laodelphax striatellus* and *Nilaparvata lugens* (nymphs)

The test is carried out with growing plants. For this purpose 4 rice plants (14–20 days old), about 15 cm in height, are planted into each of a number of pots (diameter 5.5 cm). The plants in each pot are sprayed on a rotary table with 100 ml of an aqueous emulsion formulation containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 6 days on the treated plant until the adult stage has been reached. Evaluation of percentage mortality is made 6 days after settlement. The test is carried out at about 27° C. and 60% relative humidity, and the plants are exposed to light for 16 hours.

In this test, compound 3 effects 80–100% kill against *Nilaparvata lugens*.

EXAMPLE 5

Systemic action against *Nilaparvata lugens* (water)

Rice plants which are about 10 days old and about 10 cm high are put into a plastic beaker which contains 150 ml of an aqueous emulsion formulation of the test compound in a concentration of 100 ppm and which is sealed with a perforated plastic lid. The root of each rice plant is pushed through a hole in the plastic lid into the aqueous test formulation. The rice plant is then populated with 20 nymphs of *Nilaparvata lugens* in the $N_2$–$N_3$ stage and covered with a plastic cylinder. The test is carried out at ca. 26° C. and 60% relative humidity and the plant is exposed to light for 16 hours. A mortality count is made 5 days later, using untreated controls for comparison purposes, thereby establishing whether the test compound absorbed through the root kills the test organisms on the upper parts of the plant.

In this test compounds 1 and 3 effects 80–100% kill (mortality) against *Nilaparvata lugens*.

EXAMPLE 6

Action against *Nephotettix cincticeps* (nymphs)

The test is carried out with growing plants. To this end, rice plants which are ca. 20 days old and about 15 cm in height are planted into each of a number of pots (diameter: 5.5 cm).

The plants in each pot are sprayed on a rotary table with 100 ml of an aqueous emulsion formulation containing 400 ppm of the test compound. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be watered at least once. The test is carried out at a temperature of about 24° C. and at 60% relative humidity. The plants are exposed to light for a period of 16 hours.

The compounds of formula I exhibit good activity in this test.

EXAMPLE 7

Nematocidal action against *Meloidogyne incognita*

Eggs of *Meloidogyne incognita* are mixed into sand. This mixture is then put into 200 ml earthenware pots (5000 eggs per pot). On the same day a three-week old tomato plant is planted in each pot and the formulated test compound is applied to the pots by drench application (0.0006% active ingredient, based on the volume of the soil). The potted plants are stood in a greenhouse at a temperature of 26°±1° C. and a relative humidity of 60%. After 4 weeks, evaluation is made by examining the plants for knot-root formation in accordance with the "root-knot index".

Compounds of formula I exhibit good activity against *Meloidogyne incognita* in that they substantially reduce root-knot formation.

What is claimed is:

1. A method of controlling pests selected from insects and plant-destructive nematodes, which comprises contacting or treating said pests, their different development stages or the locus thereof, with a pesticidally effective amount of a compound of formula I

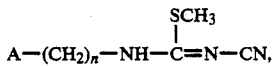 (I)

wherein A is a pyridyl, furanyl, indolyl or pyrrolyl ring, and n is 1 or 2, or with a composition which contains a pesticidally effective amount of said compound, together with adjuvants and carriers therefor.

2. Method according to claim 1, wherein in formula I n is 1.

3. Method according to claim 1, wherein in formula I A is pyrid-2-yl, pyrid-3-yl, furanyl-2-yl, indol-3-yl or pyrrol-3-yl.

4. Method according to claim 3, wherein the compound of formula I is

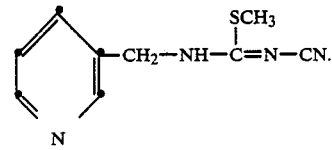

5. Method according to claim 1 for controlling plant-destructive insects.

6. Method according to claim 5 for controlling sucking insects.

* * * * *